United States Patent [19]

Kempf et al.

[11] Patent Number: 4,476,139

[45] Date of Patent: Oct. 9, 1984

[54] DISCOVERY OF ANTIBIOTIC L-681,217 IN FERMENTATION BROTH

[75] Inventors: August J. Kempf, Staten Island, N.Y.; Kenneth E. Wilson, Westfield, N.J.; Otto D. Hensens, Middletown, N.J.; Richard L. Monaghan, Somerset, N.J.; Sheldon B. Zimmerman, Springfield, N.J.; Eugene L. Dulaney, Summit, N.J.

[73] Assignee: Merck & Co., Inc., Rahway, N.J.

[21] Appl. No.: 426,585

[22] Filed: Sep. 29, 1982

[51] Int. Cl.$^3$ ............... A61K 31/35; C07D 309/04

[52] U.S. Cl. .................. 424/283; 435/118; 549/414

[58] Field of Search .................. 424/283; 542/421

[56] References Cited

PUBLICATIONS

Kishi et al., Aldrichmica Acta, 13, 23 (1980).

Primary Examiner—Nicky Chan
Attorney, Agent, or Firm—David L. Rose; Hesna J. Pfeiffer

[57] ABSTRACT

The antibiotic, L-681,217, having antibacterial and growth-permittant activity, is produced by fermentation of *Streptomyces cattleya* in a suitable nutrient media.

3 Claims, No Drawings

DISCOVERY OF ANTIBIOTIC L-681,217 IN FERMENTATION BROTH

BACKGROUND OF THE INVENTION

This invention relates to a new antibacterial and growth-permittant antibiotic agent. More particularly, the instant invention relates to a new antibacterial and growth-permittant antibiotic agent, L-681,217. The invention encompasses the antibiotic in dilute forms; as crude concentrates; in pure forms; and in formulations suitable for antibiotic and growth-permittant applications.

It is an object of the instant invention to provide a new and useful antibiotic agent with antibacterial activity and growth-permittant activity. Another object is to provide a process for preparing the novel antibiotic substance by fermentation of a nutrient medium with a microorganism identified as *Streptomyces cattleya*. Other objects will be apparent from the detailed description of the instant invention hereinafter provided.

In its composition of matter aspect, therefore, the instant invention may be described as residing in the concept of the novel antibiotic, L-681,217, having the physical and chemical characteristics hereinafter described. The instant invention is based upon applicants' discovery that L-681,217 is an antibiotic which is effective against both gram-positive and gram-negative bacteria and may be used to treat bacterial infections in humans and animals. Further, and importantly, L-681,217 may be used as a growth-permitting agent for animals such as chickens and pigs. It is contemplated that therapeutically effective amounts of antibiotic L-681,217 will be employed in antibacterial and growth-permittant applications. The antibacterial and growth-permittant activity of antibiotic L-681,217 have been confirmed by standard pharmaceutical techniques.

Antibiotic L-681,217 is obtained by growing under controlled conditions the microorganism, *Streptomyces cattleya*, in a fermentation broth. The fermentation may be carried out in media containing suspended nutrient matter or in predominantly clear media wherein the medium is substantially free of suspended nutrient matter.

Based on extensive taxonomic studies, the antibiotic producing microorganism is identified as *Streptomyces cattleya*. A useful strain is designated MA 5203 in the culture collection of MERCK & CO., Inc., Rahway, N.J. A culture thereof has been placed on permanent deposit with the culture collection of the American Type Culture Collection, 12301 Parklawn Drive, Rockville, Md. 20852, and has been assigned Accession No. ATCC 39203. Where sporulation occurs, the culture displays the distinctive orchid color of *Streptomyces cattleya* and the spiral sporophores. It has, therefore, been designated *Streptomyces cattleya*. Applicants point out, however, that it is an atypical *S. cattleya;* having on some media sectoring with areas of no aerial mycelia, poor growth on certain media, and more pigment than usual produced on tyrosine agar.

MORPHOLOGICAL AND CULTURAL CHARACTERISTICS OF *STREPTOMYCES CATTLEYA* MA 5203 (ATCC 39203)

The morphological and cultural characteristics of *Streptomyces cattleya* MA 5203 (ATCC 39203) are set forth below.

Morphology

Sporophores are spirals occurring as side and terminal branches or aerial mycelia, Spiral forms include primative loops, loose irregular coils and some compact coils.

Cultural Characteristics (V=vegetative growth; A=aerial mycelium; SP=soluble pigment)

Oatmeal agar (ISP Medium 3)
  V: Cream-colored
  A: None
  SP: None
Czapek Dox agar (sucrose nitrate agar)
  V: No growth
  A:
  SP:
Egg albumin agar
  V: Flat, spreading, colorless
  A: Moderate, white with areas of very pale orchid
  SP: None
Glycerol asparagine agar (ISP Medium 5)
  V: Reverse—tan
  A: Moderate, mixture of orchid (10 gc), pale orchid and white
  SP: Slight browning of medium
Inorganic salts-starch agar (ISP Medium 4)
  V: Poor growth, flat, spreading, colorless
  A: None
  SP: None
Yeast extract-malt extract agar (ISP Medium 2)
  V: Reverse—tan
  A: Mixture of orchid (10 gc), pale orchid and white. Some sectoring with areas of no aerial mycelia
  SP: None
Peptone-iron-yeast extract agar
  V: Moderate, cream-colored
  A: None
  SP: None
  Melanin: None
Nutrient tyrosine agar
  V: Tan
  A: None
  SP: Light rose-brown
Tyrosine Agar (ISP Medium 7)
  V: Reverse—light brown edged with white
  A: Mixture of orchid and white
  SP: Light rose-brown
Carbon utilization
  Pridham-Gottlieb basal medium+1% carbon source;
    +=growth; ±=growth poor or questionable;
    −=no growth as compared to negative control
    (no carbon source

| | |
|---|---|
| Glucose | + |
| Arabinose | + |
| Cellulose | − |
| Fructose | + |
| Inositol | + |
| Lactose | + |
| Maltose | + |
| Mannitol | + |
| Mannose | + |
| Raffinose | − |
| Rhamnose | + |
| Sucrose | + |
| Xylose | + |

Temperature range (Yeast extract-dextrose+salts agar)
28° C.: Good growth with sporulation
37° C.: Good vegetative growth with moderate aerial mycelia
50° C.: No growth
Oxygen requirement (Stab culture in yeast extract-dextrose+salts agar)
Aerobic
All readings taken after three weeks at 28° C. unless noted otherwise. pH of all media approximately neutral (6.8–7.2).
Color number designations taken from Color Harmony Manual, 1958, 4th Edition, Container Corporation of America, Chicago, Ill.

The ability to produce antibiotic L-681,217 is not unique to *Streptomyces cattleya* (ATCC 39203) as descried above. It will be apparent to those skilled in the art that other strains of *Streptomyces cattleya* also may be employed. Included among known strains of *Streptomyces cattleya* which may be employed in the preparation of antibiotic L-681,217 is, for example, *Streptomyces cattleya* NRRL 8057, Northern Regional Research Laboratories, Northern Utilization Research and Development Division, Agricultural Research Service, U.S. Department of Agriculture, Peoria, Ill. This strain is disclosed in U.S. Pat. No. 3,950,357, issued Apr. 13, 1976, where it is employed in the preparation of the antibiotic, thienamycin. It will be understood, therefore, that the instant invention includes the use of other strains of *Streptomyces cattleya* including strains either isolated from nature or obtained by mutation such as, for example, those obtained by natural selection or those produced by mutating agents, for example, X-ray irradiation, ultraviolet irradiation, nitrogen mustards and the like which, under suitable conditions will yield antibiotic L-681,217.

PREPARATION OF ANTIBIOTIC L-681,217

Antibiotic L-681,217 is produced during the aerobic fermentation of suitable aqueous nutrient media under controlled conditions via inoculation with the organism *Streptomyces cattleya* MA 5203 (ATCC 39203). Aqueous media, such as those employed for the production of other antibiotics are suitable for producing antibiotic L-681,217. Such media contain sources of carbon, nitrogen and inorganic salts assimilable by the microorganism. The choice of media is not critical and the fermentation may be carried out in media containing suspended nutrient matter or in predominantly clear media substantially free of suspended nutrient matter.

In general, carbohydrates, for example, dextrose and lactose and starches as well as glycerol, pectin and peptonized milk either alone or in combination can be used as sources of assimilable carbon in the nutrient medium. The exact quantity of the carbon source or surces utilized in the medium depends in part upon the other ingredients of the medium but, in general, the amount of carbon source usually varies between about 1% and 6% by weight of the medium. These carbon sources can be used individually or several such carbon sources can be combined in the medium.

Many proteinaceous materials may be used as nitrogen sources in the fermentation process. Suitable nitrogen sources include, for example, yeast extract, yeast hydrolysates, soybean flour, distillers solubles, corn steep, peptonized milk, lard water, peanut meal and tomato paste and the like. The sources of nitrogen, either alone or in combination, are used in amounts ranging from about 0.2% to 6% by weight of the aqueous medium.

Among the nutrient inorganic salts which may be incorporated in the medium are the customary salts capable of yielding sodium, potassium, ammonium, calcium, magnesium, phosphate, sulfate, chloride, carbonate and the like ions. Also, there may be included trace metals such as cobalt, manganese and iron.

The fermentation is carried out at temperatures ranging from about 20° C. to 37° C.; however, for optimum results it is preferred to conduct the fermentation at temperatures of from about 24° C. to 32° C. The pH of the nutrient media suitable for growing *Streptomyces cattleya* MA 5203 (ATCC 39203) culture and producing antibiotic L-681,217 should be in the range of from about 4.0 to 7.0.

Small scale fermentation of the antibiotic conveniently is carried out by inoculating a suitable nutrient medium with the antibiotic-producing culture and, after transfer to a production medium, permitting fermentation to proceed at a constant temperature of about 28° C. on a shaker for several days. At the end of the incubation period, the antibiotic activity is isolated from the fermentation broth by techniques hereinafter described.

The small scale fermentation may be conducted in a sterilized flask via a one, two, three or four-stage seed development. The nutrient medium for the seed stage may be any suitable combination of carbon and nitrogen sources. The seed flask is shaken in a constant temperature chamber at about 28° C. until maximum growth is completed (usually 1–3 days) and some of the resulting growth is used to inoculate either a further seed-stage or the production medium. Intermediate stage seed-flasks, when used, are developed essentially in the same manner; that is, part of the contents of the flask is used to inoculate either the next stage seed medium or the production medium. The inoculated production flasks are shaken at a constant temperature (about 28° C.) for several days (usually 3 to 5 days) and at the end of the incubation period the antibiotic L-681,217 is isolated.

For large scale work, it is preferable to conduct the fermentation in suitable tanks provided with an agitator and a means of aerating the fermentation medium. The nutrient medium is made up in the tank and sterilized by heating to about 120° C. Upon cooling, the sterilized medium is inoculated with a previously grown seed culture of the producing organism and fermentation is permitted to proceed for a period of several days (3 to 5 days, for example) while agitating and/or aerating the nutrient medium and maintaining the temperature at about 28° C.

A preferred process for preparing antibiotic L-681,217 is set forth below.

MEDIUM PREPARATION

Medium A (seed medium) is prepared by dissolving the ingredients shown below in distilled water and adjusting the pH to between 7.0 and 7.2 with concentrated hydrochloric acid or 50% aqueous sodium hydroxide before sterilization. Forty-four ml of this medium are dispensed into 250 ml, three-baffled shake flasks and 500 ml of the same medium are dispensed into 2000 ml, three-baffled shake flasks. The flasks are plugged with cotton, sterilized by heating in an autoclave at 121° C. for 25 minutes, and allowed to cool to room temperature.

| Medium A (Seed Medium) | |
|---|---|
| Ingredient | Concentration (% by weight) |
| Dextrose | 0.1 |
| Soluble Starch | 1.0 |
| Beef Extract | 0.3 |
| Ardamine pH (Yeast Products, Inc. Clifton, N.J.) | 0.5 |
| NZ Amine Type E (Humko-Sheffield Co., Norwich, N.Y.) | 0.5 |
| $MgSO_4.7H_2O$ | 0.005 |
| Phosphate Buffer | 2.0 ml |
| $KH_2PO_4$ | 9.1% by weight |
| $Na_2HPO_4$ | 9.5% by weight |
| $CaCO_3$ (added after pH is adjusted to appropriate value) | 0.05 |
| pH | 7.0 |

Medium B (production medium) is prepared by suspending the ingredients listed below in distilled water, adjusting the pH to between 7.0 and 7.2 with concentrated hydrochloric acid or 50% aqueous sodium hydroxide before sterilization and sterilizing by heating at 121° C., 18 psi, for twenty minutes. Four 14-liter magnetically coupled Microferm fermentors (New Brunswick Scientific Co., Inc., Edison, N.J.) are sterilized with 100 ml distilled water in the jar by heating in an autoclave at 121° C., 18 psi, for 90 minutes. Nine and one-half liters of cooled Medium B from the nutrient sterilizer are aseptically transferred to the sterile fermentors and the temperature is adjusted to about 28° C.

| Medium B (Production Medium) | |
|---|---|
| Ingredient | Concentration (% by weight) |
| Dextrose | 1.0 |
| Asparagine | 0.1 |
| $K_2HPO_4$ | 0.01 |
| $MgSO_4.7H_2O$ | 0.05 |
| Yeast Extract | 0.05 |
| $FeSO_4.7H_2O$ | $1.0 \times 10^{-5}$ |
| $MnSO_4.H_2O$ | $1.0 \times 10^{-5}$ |
| $CuCl_2.2H_2O$ | $2.5 \times 10^{-7}$ |
| $CaCl_2$ | $1.0 \times 10^{-6}$ |
| $H_3BO_3$ | $5.6 \times 10^{-7}$ |
| $(NH_4)_6Mo_7O_{24}.4H_2O$ | $2.0 \times 10^{-6}$ |
| $CaCO_3$ | 0.3 |

CULTURE DEVELOPMENT

Seed Stage

A lyophile of *Streptomyces cattleya* MA 5203 (ATCC 39203) is opened aseptically and is used to inoculate a 250 ml flask of Medium A prepared as described above. The flask is incubated at 28° C. for 49 hours on a 220 rpm rotary shaker. Inoculum development is continued by aseptically transferring 2 ml from the first flask into each of four additional 250 ml flasks of Medium A. These four flasks are incubated at 28° C. for 24 hours on a 220 rpm rotary shaker. After 24 hours, the four flasks are pooled and 15 ml is aseptically transferred to each of four 2000 ml shake flasks of Medium A. The 2000 ml shake flasks are incubated at 28° C. for 24 hours on a 220 rpm rotary shaker. Packed cell volumes and pH measurements on the seed stages range from 12 to 19% and from 7.5 to 7.8, respectively.

Production Stage

One 2000 ml flask is used to inoculate each of the 14-liter vessels prepared as described above. The fermentation conditions, set immediately after inoculation, are 28° C. (27.6°–28.2° C.), 400 rpm, and 3 liters/minute air, corresponding to a Kd of $3.8 \times 10^{-4}$ gram.moles $O_2$/ml/hr/atm. Antifoam agent (Polyglycol P-2000) is added as necessary to control foam but does not exceed 0.06%. All fermentors are harvested 90 hours post inoculation. Antibacterial (standard disc assay) and pH analyses are performed on fermentor whole broth time samples and the results are shown below, averaged for the four 14-liter batches.

| Age (hours) | pH | Antibiotic Activity* ATCC 8461 | vs. *Vibrio percolans* |
|---|---|---|---|
| 0 | 6.8 | 0 | |
| 6 | 7.1 | 0 | |
| 18 | 6.9 | 0 | |
| 30 | 6.8 | 12.25 | |
| 42 | 6.7 | 18.25 | |
| 54 | 6.8 | 22.5 | |
| 66 | 6.0 | 23.75 | |
| 78 | 5.8 | 26.75 | |
| 90 | 6.2 | 30 | |

*mm zones from ¼" discs, 10 µl/disc

Although the production media described above is a preferred media for production of antibiotic L-681,217, a wide variety of production media may be employed. Typical of other useful media, for example, are the following.

| Production Media | |
|---|---|
| Ingredient | Concentration (gm/l) |
| 1. Corn Steep Liquor | 15.0 |
| $(NH_4)_2SO_4$ | 4.0 |
| $CaCO_3$ | 6.0 |
| CPC Industrial Starch Mod. (Corn Products Int., Englewood Cliffs, N.J.) | 20.0 |
| Corn Meal | 1.0 |
| Soybean Meal | 4.0 |
| Dextrose | 5.0 |
| $KH_2PO_4$ | 0.3 |
| Soybean Oil | 2.5 ml |
| Distilled Water | 1000.0 ml |
| pH 6.7 | |
| 2. Corn Meal | 20.0 |
| Distiller's Solubles | 10.0 |
| Soybean Meal | 15.0 |
| Sodium Citrate | 4.0 |
| $CaCl_2.2H_2O$ | 0.5 |
| $MgSO_4.7H_2O$ | 0.1 |
| $CoCl_2.16H_2O$ | 0.01 |
| $FeSO_4.7H_2O$ | 0.01 |
| Polyglycol P-2000 (Dow Chemical Co., Midland, Michigan) | 2.5 ml |
| Distilled Water | 1000 ml |
| pH 6.5 | |

ISOLATION OF ANTIBIOTIC L-681,217

Thirty-four liters of whole broth (4 × 14 liter batches obtained above) are combined, filtered with a filter aid and washed with water to original volume. The combined filtrate and wash containing 5.0 gm of antibiotic L-681,217 by analytical HPLC, is adsorbed at pH 7 on 3.7 liters of Amberlite XAD-2 resin at 200 ml/min. The column is washed with 6 liters of deionized water, then eluted with 8 liters of 20/80 acetone/water and 10 liters of 60/40 acetone/water. Fractions are collected as follows: fractions 1 and 2 (4 liters each) and fractions 3–7 (2 liters each). Fractions 2–4, containing 5.0 gm of antibiotic L-681,217, are combined and evaporated to 1 liter at pH 7.0. Fifteen ml of 1 M citric acid is added to adjust the pH to 3.4. The solution is extracted with two 1 liter volumes of ethyl acetate. The ethyl acetate extracts are combined, dried with anhydrous sodium sulfate, evaporated finally into water at pH 7.5 and lyophilized to give 5.2 gm of powder (84% pure based on HPLC).

Five hundred mg of lyophilized powder obtained above is dissolved in 50/50 methanol/0.05 M sodium citrate pH 3.3 (total volume=3.7 ml) and applied to a DuPont Zorbax ODS (25 cm×2.12 cm) prep C18 column equilibrated with 50/50 methanol/0.05 M sodium citrate pH 3.3. The flow rate initially is 1 ml/min until the sample is onto the column, then gradually is increased to 10 ml/min. The eluate is 50/50 methanol/0.05 M sodium citrate pH 3.3. After a 50 ml forecut, 15 ml fractions are collected and assayed by HPLC and bioassay. Based on the assays, fractions 24 through 45, containing essentially pure antibiotic L-681,217, are combined and concentrated to remove the methanol. The resulting aqueous rich cut is adjusted to pH 5.0 and extracted twice with an equal volume of ethyl acetate. The combined extracts are dried with anhydrous sodium sulfate and concentrated finally into water at pH 6.5. A small amount of methanol is added to help solubilize the antibiotic L-681,217. The methanol-water solution is lyophilized to give 174 mg of antibiotic L-681,217.

The reverse phase HPLC assay, employed analytically above, is carried out using a DuPont Zorbax ODS column (4.6 mm O.D.×25 cm) at ambient temperature. The solvent system is 40/60 methanol/0.01 M potassium phosphate at pH 7. The flow rate is 1.2 ml/min and column effluent is monitored at 288 nm. Peak areas are calculated using a Spectra-Physics Autolab System I Computing Integrator. The retention time for antibiotic L-681,217 was 716 seconds.

PHYSICAL CHARACTERISTIC OF ANTIBIOTIC L-681,217

1. Mass Spectral (MS) Data (L-681,217)

The compound did not afford useful mass spectra underivatized. As the trimethylsilyl derivative (TMS), a weak molecular ion was observed at m/z 1019 as a penta-TMS derivative (m/z 1064, D-TMS). The empirical formula corresponding to an underivatized M-H$_2$O species was determined as C$_{36}$H$_{51}$NO$_9$ by high resolution peak matching (calc for C$_{36}$H$_{51}$NO$_9$+(C$_3$H$_8$Si)$_4$—CH$_3$ 914.4910, found 914.4905). The molecular weight and elemental composition of L-681,217 are therefore 659 and C$_{36}$H$_{53}$NO$_{10}$, respectively.

The methyl ester derivative of L-681,217, by FAB (Fast Atom Bombardment), indicated a strong molecular ion peak at m/z 673 (LiCl spike m/z 680; NaCl spike m/z 696). EI (Electron Impact) spectra afforded a highest mass ion at m/z 655 corresponding to C$_{37}$H$_{53}$NO$_9$ (calc 655.3720, found 655.3720), which is M-H$_2$O for the monomethyl ester of L-681,217. Additional significant ions were observed at m/z 559 (calc. for C$_{31}$H$_{45}$NO$_8$ 559.3145, found 559.3144; M—H$_2$O—C$_6$H$_8$O), 527 (calc for C$_{30}$H$_{41}$NO$_7$ 527.2883, found 527.2885; 559—CH$_3$OH), 497 (calc for C$_{29}$H$_{39}$NO$_6$ 497.2777, found 497.2777; 559—H$_2$O—C$_2$H$_4$O), 465 (calc for C$_{28}$H$_{35}$NO$_5$ 465.2515, found 465.2514; 497—CH$_3$OH), and 123 (calc for C$_8$H$_{11}$O 123.0810, found 123.0810).

2. 13C NMR Chemical Shifts (L-681,217)

The spectrum was recorded in CD$_3$OD/CDCl$_3$ (1:4) solution at 18° C. (18.5 mg in 0.35 ml). Chemical shifts are given in ppm downfield of internal tetramethylsilane (TMS) standard. In agreement with the mass spectral data, 36 carbon atoms are observed with the following chemical shifts: 9.9, 10.7, 12.0, 12.9, 13.5, 21.0, 39.0, 39.2, 40.0, 41.5, 56.2, 56.6, 72.0, 74.4, 74.6, 74.8, 77.8, 84.3, 89.7, 98.7, 125.9, 126.2, 127.0, 128.2, 128.6, 129.3, 129.5, 129.7, 131.5, 133.0, 133.6, 136.5, 138.8, 142.9, 173.3, 176.0 ppm.

Antibiotic L-681,217 is believed to have the following structure.

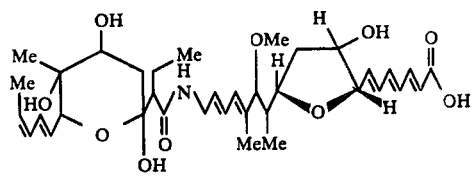

BIOLOGICAL CHARACTERISTICS OF ANTIBIOTIC L-681,217

Antibacterial Activity

Antibiotic L-681,217 shows activity against a variety of gram-positive and gram-negative organisms. Activity is confirmed in vitro by standard disc plate techniques. A typical assay is carried out as described below.

Antibacterial Spectrum Profile (Antibiotic L-681,217)

A 255 μ/ml solution of antibotic L-681,217 in 10%–90% (v/v) methanol-distilled water is employed as the test sample. A droplet of 0.015 ml of test sample is placed on the surface of nutrient agar susceptibility plates which have been seeded with standardized suspensions of test organisms. The plates are read (zone of inhibition measured) after overnight incubation. A solution of 10%/90% (v/v) methanol-distilled water gives no zone of inhibition. Typical results are shown below.

| (Organism, MB NO.* ATCC NO.) | Inhib. Zone Diam. (mm) Antibiotic L-681,217 255 μg/ml |
|---|---|
| Bacillus sp. 633 | 12 |
| Proteus vulgaris 1012 | 13 |
| Staphylococcus aureus 108 (6538 P) | 10 |
| Bacillus subtilis 964 (6633) | 12 |
| Sarcina lutea 1101 (9341) | 25 |
| Brucella bronchiseptica 965 (4617) | 13 |
| Vibrio percolans 1272 (8461) | 18 |
| Xanthomonas vesicatoria 815 | 15 |
| Proteus vulgaris 838 (21100) | 16 |
| Escherichia coli 1418 | 16 |
| Pseudomonas stutzeri 1231 (11607) | 0 |
| Klebsiella pneumoniae 1264 | 18 |
| Enterobacter aerogenes 835 | 15 |
| Erwinia atroseptica 1159 (4446) | 0 |
| Pseudomonas aeruginosa 2824 | 12 H** |
| Corynebacterium pseudodiphtheriticum 261 | 12 |
| Escherichia coli 60 (9637) | 17 |
| Streptococcus faecium 2820 | 18 |
| Streptococcus agalactiae 2875 | 10 |

| (Organism, MB NO.* ATCC NO.) | Inhib. Zone Diam. (mm) Antibiotic L-681,217 255 μg/ml |
|---|---|
| *Proteus vulgaris* 2112 (episome) | 18 |
| *Proteus mirabilis* 3126 | 10 H** |

*MB No.—Merck Bacteria No.
**H = hazy

Antibiotic L-681,217 clearly demonstrates activity against gram-positive and gram-negative organisms.

When used as an antibiotic, L-681,217 may be employed in the form of pharmaceutical preparations which contain it in admixture or conjunction with an organic or inorganic solid or liquid pharmaceutical excipient suitable for internal, parenteral or local administration. Suitable excipients are substances that do not react with the antibiotic, for example, water, gelatin, lactose, starches, stearyl alcohol, magnesium stearate, talcum, vegetable oils, benzyl alcohols, gums, propylene glycols, polyalkylene glycols, white petroleum jelly, cholesterol or other known pharmaceutical excipients. The pharmaceutical formulations may be, for example, tablets, dragees, ointments, creams or capsules, or in liquid form solutions, suspensions or emulsions. They may be sterilized and/or contain assistants such as preserving, stabilizing, wetting or emulsifying agents, solution promoters, salts for regulating osmotic pressure or buffers.

Where it is desired to administer the antibiotic in dry, solid unit dosage form, capsules, boluses or tablets containing the desired amount of antibiotic are employed. These dosage forms are prepared by intimately and uniformly mixing the active ingredient with suitable finely divided diluents, fillers, disintegrating agents and/or binders such as, for example, starch, lactose, talc, magnesium stearate, vegetable gums and the like. Such unit dosage formulations may be varied widely with respect to their total weight and content of antibiotic L-681,217 depending upon factors such as the type of host to be treated, the severity and type of infection to be treated and the weight of the host. Conveniently, the antibiotic may be administered on a daily basis at from about 5 to about 100 mg per kilogram of body weight.

Growth Permittant Activity

In order to evaluate the growth permittant activity of antibiotic L-681,217, the antibiotic is tested in chicks by the technique described below.

Antibiotic L-681,217 is tested in the 9-day Chick Growth Permittant Test. Day old broiler chicks are employed. The chicks are fed a soybean-sucrose semi-synthetic diet either unsupplemented or supplemented with 2.5, 5, 10 or 20 ppm of the antibiotic. The diet and water were available ad libitum throughout the test period. Typical results are shown in the following table.

| Treatment Compound | Level (ppm) | No. Chicks Dead/Total | 9 Day Wt. Gains | Rel. % | Feed/Gain g/g | Rel. % |
|---|---|---|---|---|---|---|
| None | — | 0/64 | 88.3 ± 19.1 | — | 1.544 | — |
| L-681,217 | 2.5 | 1/16 | 97.7 ± 16.3 | +11 | 1.271 | −18 |
|  | 5 | 0/16 | 90.1 ± 14.0 | + 2 | 1.482 | − 4 |
|  | 10 | 0/16 | 96.9 ± 14.7 | +10 | 1.408 | − 9 |
|  | 20 | 1/16 | 102.9 ± 15.5 | +17 | 1.339 | −13 |

Thus it is clear that antibiotic L-681,217 displays significant growth-permittant activity; i.e., effective in permitting an animal to grow toward its full genetic potential. Antibiotic L-681,217, therefore, may be used as a feed additive to permit the growth of monogastric animals such as chickens and swine. When so used, antibiotic L-681,217 shortens the time required for bringing animals up to marketable weight.

When antibiotic L-681,217 is used as a component of animal feed, it is first formulated as a feed supplement. In such feed supplements, antibiotic L-681,217 is present in relatively concentrated amounts intimately dispersed in an inert carrier or diluent. The feed supplement can be added to the feed or made into a premix by an intermediate dilution or blending step. By inert carrier is meant one that may be administered safely to animals. Preferably, the carrier is one that is, or may be, an ingredient of the animal ration. Typical carriers or diluents suitable for such compositions include, for example, distiller's dried grains, corn meal, citrus meal, fermentation residues, ground oyster shells, wheat shorts, molasses solubles, corn cob meal, edible bean mill feed, soya grits, crushed limestone and the like.

The antibiotic is intimately dispersed throughout the carrier by methods such as grinding, stirring, milling or tumbling. Compositions containing about 50,000 to 500,000 ppm of the antibiotic are particularly suitable as feed supplements.

Examples of typical feed supplements containing antibiotic L-681,217 dispersed in a solid carrier are:

| Ingredient | Concentration (% by weight) |
|---|---|
| (A) L-681,217 | 5.0 |
| Wheat Standard Middling | 95.0 |
| (B) L-681,217 | 50.0 |
| Corn Distiller's Grains | 50.0 |

These and similar feed supplements are prepared by uniformly mixing the antibiotic with the carrier.

The feed supplement can be added directly to the feed or made into a premix by an intermediate dilution or blending step with an orally ingestible carrier. Compositions containing 300 to 5000 ppm of the antibiotic are particularly suitable as premixes. The premixes are prepared by uniformly mixing the antibiotic with an orally ingestible carrier.

Such supplements or premixes are added to the animal feed in an amount to give the finished feed the concentratin of antibiotic L-681,217 desired for growth permittant activity. In chickens and swine, antibiotic L-681,217 usually is fed at a final concentration of between 10-100 ppm of feed in order to achieve the desired growth permittant result. It will be understood by those skilled in this art that special feed supplement formulations and finished animal feeds containing antibiotic L-681,217 may also include vitamins, other antibiotics and growth permitting agents and other nutritional substances.

Included within the scope of this invention are the non-toxic, pharmaceutically acceptable salts of antibiotic L-681,217. Such salts include, for example, the alkali metal and alkaline earth metal salts such as those derived from sodium, potassium or calcium or salts derived from ammonium, or salts derived from organic bases such as triethylamine, N-ethylpiperidine, dibenzylethylenediamine and the like.

What is claimed is:

1. The compound L-681,217 of the structure:

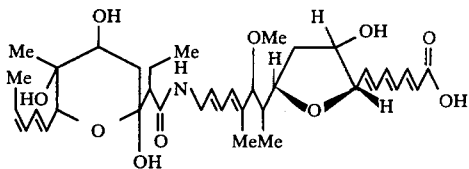

and the pharmaceutically acceptable salts thereof.

2. An antibiotic composition comprising an antibiotically effective amount of antibiotic L-681,217 or a pharmaceutically acceptable salt thereof and a pharmaceutically acceptable carrier.

3. A growth-permittant composition comprising a growth-permitting amount of antibiotic L-681,217 or a pharmaceutically acceptable salt thereof and a pharmaceutically acceptable carrier.

* * * * *